(12) United States Patent
Rack et al.

(10) Patent No.: US 9,126,905 B2
(45) Date of Patent: Sep. 8, 2015

(54) PROCESS FOR MANUFACTURING FLUOROAROMATICS

(71) Applicant: BASF SE, Ludwigshafen (DE)

(72) Inventors: Michael Rack, Eppelheim (DE); Maximilian Dochnahl, München (DE); Volker Maywald, Ludwigshafen (DE); Bernd Wolf, Niederkirchen (DE); Joachim Gebhardt, Wachenheim (DE); Timo Frassetto, Mannheim (DE); Uwe Josef Vogelbacher, Ludwigshafen (DE); Roland Götz, Neuluβheim (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 14/415,265

(22) PCT Filed: Jul. 8, 2013

(86) PCT No.: PCT/EP2013/064361
§ 371 (c)(1),
(2) Date: Jan. 16, 2015

(87) PCT Pub. No.: WO2014/012811
PCT Pub. Date: Jan. 23, 2014

(65) Prior Publication Data
US 2015/0166446 A1    Jun. 18, 2015

Related U.S. Application Data

(60) Provisional application No. 61/672,787, filed on Jul. 18, 2012.

(30) Foreign Application Priority Data

Jul. 18, 2012 (EP) .................................. 12176859

(51) Int. Cl.
| | | |
|---|---|---|
| *C07C 37/62* | (2006.01) | |
| *C07C 37/76* | (2006.01) | |
| *C07C 17/35* | (2006.01) | |
| *C07C 17/093* | (2006.01) | |
| *C07C 41/22* | (2006.01) | |
| *C07C 51/363* | (2006.01) | |
| *C07C 209/74* | (2006.01) | |
| *C07D 213/73* | (2006.01) | |

(52) U.S. Cl.
CPC ............ *C07C 37/62* (2013.01); *C07C 17/093* (2013.01); *C07C 17/35* (2013.01); *C07C 37/76* (2013.10); *C07C 41/22* (2013.01); *C07C 51/363* (2013.01); *C07C 209/74* (2013.01); *C07D 213/73* (2013.01)

(58) Field of Classification Search
None
See application file for complete search history.

(56) References Cited

U.S. PATENT DOCUMENTS

| 2,563,796 | A |   | 8/1951 | Shenk, Jr. et al. | |
|---|---|---|---|---|---|
| 3,160,623 | A |   | 12/1964 | Anello et al. | |
| 4,812,572 | A | * | 3/1989 | Howarth et al. | 546/290 |
| 4,831,148 | A | * | 5/1989 | Schurter et al. | 546/345 |
| 4,886,920 | A | * | 12/1989 | Cantrell | 570/141 |
| 4,912,268 | A | * | 3/1990 | Krackov et al. | 570/141 |
| 5,107,046 | A | * | 4/1992 | Cantrell | 570/141 |
| 6,179,970 | B1 | * | 1/2001 | Coe et al. | 204/157.62 |

OTHER PUBLICATIONS

Database CAPLUS in STN, Acc. No. 1987:175936, Begemann et al., DE 3520316 A1 (Dec. 11, 1986) (abstract).*
Database CAPLUS in STN, Acc. No. 1991:655777, Yoda et al., JP 03167143 A (Jul. 19, 1991) (abstract).*
International Search Report, PCT/EP2013/064361, filed Jul. 8, 2013, search completed Sep. 6, 2013.
International Preliminary Report on Patentability, PCT/EP2013/064361, filed Jul. 8, 2013, report issued Jan. 20, 2015.
Ferm et al., "Synthesis of Aromatic Flourides Through Diazotization in Anhydrous Hydrogen Flouride", Journal of the American Chemical Society, vol. 72, No. 10, Oct. 19, 1950, pp. 4809-4810.
Yoneda et al., "Facile Preparation of Aromatic Fluorides by Deaminative Fluorination of Aminoarenes Using Hydrogen Fluoride Combined with Bases", Tetrahedron, vol. 52, No. 1, Jan. 1, 1996, pp. 23-36.

* cited by examiner

*Primary Examiner* — Brian J Davis
(74) *Attorney, Agent, or Firm* — Brinks Gilson & Lione

(57) ABSTRACT

The present invention relates to a process for manufacturing fluoroaromatics of formula (I),

A-F         (I)

comprising
step a) diazotization of aminoaromatics of formula (II) in anhydrous HF with an aqueous solution of a diazotizing agent; followed by
step b) thermic decomposition of the diazonium salt of formula (III) resulting from step a);
wherein the variables are defined according to the description.

13 Claims, No Drawings

PROCESS FOR MANUFACTURING FLUOROAROMATICS

This application is a National Stage application of International Application No. PCT/EP2013/064361, filed Jul. 8, 2013, which claims the benefit of U.S. Provisional Application No. 61/672,787, filed Jul. 18, 2012, the entire contents of which are hereby incorporated herein by reference. This application also claims priority under 35 U.S.C. § 119 to EP Patent Application No. 12176859.2, filed Jul. 18, 2012, the entire contents of which is hereby incorporated herein by reference.

The invention relates to a process for manufacturing fluoroaromatics of formula (I), which are valuable intermediated in various chemical manufacturing processes.

Ferm et al. (J. of Am. Chem. Soc. 1950, 72, 4809) discloses a synthesis of 3-fluorophenol from 3-aminophenol with solid anhydrous $NaNO_2$ in the presence of HF followed by thermic decomposition with a yield of 46%. Hence, there is still room for improvement.

Yoneda et al. (Tetrahedron 1996, 52, 23-36) discloses a synthesis of 3-fluorophenol from 3-aminophenol with solid anhydrous $NaNO_2$ in the presence of pyridine/HF complex.

This process requires the use of large amounts of pyridine/HF complex, which tends to difficulties in the technical scale up. Hence, there is also still room for improvement, specifically in view of technical and economic aspects.

It is an object of the present invention to provide an efficient process for manufacturing fluoroaromatics of formula (I).

Surprisingly it has been found that fluoroaromatics of formula (I) can be prepared by diazotization of aminoaromatics of formula (II) in anhydrous HF with an aqueous solution of a diazotizing agent, followed by thermic decomposition of the diazonium salt resulting from step a).

Accordingly, the present invention relates to a process for manufacturing fluoroaromatics of formula (I), $$A\text{-}F \quad (I)$$

wherein
A is aryl or 5- or 6-membered heteroaryl,
which independently from one another both are unsubstituted or substituted by one to five substituents selected from the group consisting of halogen, $C_1$-$C_6$-alkyl, $C_2$-$C_6$-alkenyl, $C_2$-$C_6$-alkynyl, $C_1$-$C_6$-haloalkyl, $C_3$-$C_6$-haloalkenyl, $C_3$-$C_6$-haloalkynyl, hydroxy, $C_1$-$C_6$-alkoxy, amino, ($C_1$-$C_6$-alkyl)amino and di($C_1$-$C_6$-alkyl)amino;
comprising
step a) diazotization of aminoaromatics of formula (II), $$A\text{-}NH_2 \quad (II)$$

wherein A is defined as in formula (I);
in anhydrous HF with an aqueous solution of a diazotizing agent; followed by
step b) thermic decomposition of the diazonium salt of formula (III)

$$A\text{-}N_2^{+}F^{-} \quad (III)$$

resulting from step a).

The organic moieties mentioned in the definition of the compounds and the substituents according to the invention, esp. of variable A are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:
aryl: a mono- to trinuclear aromatic carbocycle having 6 to 14 ring members, such as for example phenyl, naphthyl, anthracenyl and phenanthrenyl;
5- or 6-membered heteroaryl: an aromatic 5- or 6-membered monocyclic heterocycle which, in addition to carbon atoms comprises one to three nitrogen atoms, one or two nitrogen atoms and one sulfur atom, one nitrogen and one oxygen atom, one oxygen atom, or one sulfur atom as ring members, for example 5-membered aromatic rings such as like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); and for example 6-membered aromatic rings such as pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl).

$C_1$-$C_4$-alkyl: for example $CH_3$, $C_2H_5$, n-propyl, and $CH(CH_3)_2$ n-butyl, $CH(CH_3)$-$C_2H_5$, $CH_2$—$CH(CH_3)_2$ and $C(CH_3)_3$;

$C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2- dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: a $C_3$-$C_6$-alkenyl radical as mentioned above, and also ethenyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxybutoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methyl-propyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)-amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methyl-propyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl- N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methyl-pentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)-amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

The process according to the invention comprises two steps—a diazotizing step (step a) and a thermic decomposition step (step b):

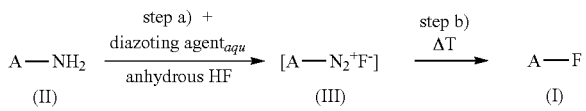

In step a) aminoaromatics of formula (II) are reacted in anhydrous HF with an aqueous solution of a diazotizing agent to give the respective intermediate diazonium salts of formula (III), which are not isolated.

The diazotization of aminoaromatics of formula (II) in anhydrous HF with an aqueous solution of a diazotizing agent is usually carried out at from −20° C. to the boiling point of the reaction mixture, preferably at from −15° C. to −10° C., particularly preferably at from −10° C. to 5° C.

Suitable diazotizing agents include, for example, nitrites such as sodium nitrite ($NaNO_2$) or potassium nitrite ($KNO_2$), and nitrosyl halogenides such as nitrosyl chloride (NOCl) or nitrosyl fluoride (NOF).

Preferred diazotizing agents are nitrites.

Also preferred diazotizing agents are alkali metal nitrites and nitrosyl halogenides;
particularly preferred alkali metal nitrites;
especially preferred $NaNO_2$ and $KNO_2$;
more preferred $NaNO_2$;
also more preferred $KNO_2$.

Also particularly preferred diazotizing agents are nitrosyl halogenides;
especially preferred NOCl and NOF;
more preferred NOCl;
also more preferred NOF.

In one embodiment of the process according to the invention, the diazotizing agent is used in excess with regard to the aminoaromatics of formula (II).

In another embodiment of the process according to the invention, the diazotizing agent and the aminoaromatics of formula (II) are used in equimolar amounts.

Preferably the amount of diazotizing agent used is at from 1 to 1.5 mole equivalents, very preferably at from 1 to 1.3 mole equivalents, more preferably at 1 to 1.1 mole equivalents, based on the amount of aminoaromatics of formula (II).

Prior to the reaction with the aminoaromatics of formula (II), the diazotizing agents are dissolved in water.

In one embodiment of the process according to the invention, the HF is used in excess with regard to the aminoaromatics of formula (II).

In another embodiment of the process according to the invention, the amount of HF used is at least 2 mole equivalents based on the amount of aminoaromatics of formula (II).

Preferably the amount of HF used is at from 10 to 30 mole equivalents, very preferably at from 15 to 27 mole equivalents, more preferably at 20 to 24 mole equivalents, most preferably 24 mole equivalents, based on the amount of aminoaromatics of formula (II).

The reaction may in principle be carried out in substance.

However, it is also possible reacting the aminoaromatics of formula (II) in anhydrous HF with an aqueous solution of a diazotizing agent in an organic solvent.

Suitable in principle are all solvents which are capable of dissolving the aminoaromatics of formula (II) and the diazotizing agent at least partly and preferably fully under reaction conditions.

Preferably step a) of the reaction according to the invention is carried out in substance without any further solvent.

In a preferred embodiment of the process according to the invention, the aminoaromatics of formula (II) and the HF are initially charged in a reaction vessel, and subsequently the aqueous solution of the diazotizing agent is added, more preferably are added a little at a time, into the reaction vessel.

It may be advantageous to add the diazotizing agent offset over a period of time.

In a further preferred embodiment of the invention, the majority, in particular at least 80% and more preferably the entirety or virtually the entirety (>95%) of the aminoaromatics of formula (II) initially charged into the HF, and the majority, in particular at least 80% and more preferably the entirety or virtually the entirety (>95%) of the aqueous solution of the diazotizing agent is added thereto under reaction conditions in the course of the reaction, for example over a period of from 0.5 to 20 h and in particular from 1 to 10 h.

Step a) of the reaction according to the invention can be carried out at atmospheric pressure, reduced pressure or under elevated pressure, if appropriate under an inert gas, continuously or batchwise.

In a preferred embodiment of the invention step a) is carried out at atmospheric pressure.

The completion of the reaction of step a) is determined via control of the temperature of the reaction mixture, which remains constant or decreases when the reaction is finished.

In step b) the intermediate diazonium salts of formula (III) obtained in step a) are thermically decomposed.

The decomposition of the intermediate diazonium salts of formula (III) is usually carried out at a temperature from 5° C.

to the boiling point of the reaction mixture, preferably from 10° C. to 80° C., particularly preferably at from 15° C. to 55° C.

Step b) of the reaction according to the invention can be carried out at atmospheric pressure, reduced pressure or under elevated pressure, if appropriate under an inert gas, continuously or batch-wise.

In a preferred embodiment of the invention step b) is carried out under elevated pressure, e.g. in a pressure vessel.

The completion of the reaction of step b) is determined via $N_2$ liberation, which is finished when the reaction is completed.

The end of the reaction can easily be determined by the skilled worker by means of routine methods.

After completion or partial completion of the reaction, the reaction mixture can be worked up by the methods customary for the purpose by means of standard techniques. Examples thereof include filtration, aqueous work-up, and evaporation of solvents and/or other volatile compounds. These methods can also be combined with each other.

In general the solvent used is removed by customary methods, distillatively for example. The crude product can then be taken up in a non-water-miscible organic solvent, any impurities extracted with unacidified or acidified water, and the system can then be dried and the solvent removed under reduced pressure.

For further purification it is possible to employ the typical methods such as distillation, rectification, crystallization, precipitation (for example by addition of an apolar solvent such as pentane, cyclohexane, heptane or toluene, or mixtures of said solvents) or chromatography.

In a preferred embodiment of the invention, after completion or partial completion of step b), the reaction mixture is worked up by steam distillation.

In another preferred embodiment of the invention, after completion or partial completion of step b), the reaction mixture is worked up by steam distillation followed by extraction with a suitable solvent.

Examples of solvents suitable for extraction are
aliphatic hydrocarbons such as pentane, hexane, cyclohexane, nitromethane and mixtures of $C_5$-$C_8$-alkanes,
aromatic hydrocarbons such as benzene, chlorobenzene, tolene, cresols, o-, m- and p-xylene, mesitylene and benzotrifluoride;
halogenated hydrocarbons such as dichloromethane, 1,2-dichloroethane, chloroform, carbon tetrachloride and chlorobenzene,
ethers such as diethyl ether, diisopropyl ether, tert.-butyl methylether (TBME), dioxane, anisole and tetrahydrofuran (THF), and
esters such as ethyl acetate and butyl acetate.

Preferred solvents for extraction are chlorbenzene, toluene, benzotrifluoride, fluorobenzene, dichloromethane and 1,2-dichloroethane.

More preferred solvents are toluene, benzotrifluoride, fluorobenzene, dichloromethane and 1,2-dichloroethane.

It is also possible to use mixtures of the solvents mentioned.

In one preferred variant of the reaction in the process according to the invention, after completion or partial completion of step b), the reaction mixture is worked up by steam distillation and the pH of the distillate resulting from steam distillation is adjusted to pH=2-7, particularly preferred 3-6, especially preferred 4-5, more preferred 4-4.5 by addition of the respective amount of a suitable base.

Aqueous mineral bases suitable for this purpose are aqueous mineral bases known to the skilled worker, for example alkali metal and alkaline earth metal hydroxides, and other metal hydroxides, such as lithium hydroxide, sodium hydroxide, potassium hydroxide, magnesium hydroxide, calcium hydroxide and aluminum hydroxide;
alkali metal and alkaline earth metal oxide, and other metal oxides, such as lithium oxide, sodium oxide, potassium oxide, magnesium oxide, calcium oxide and magnesium oxide, iron oxide, silver oxide;
alkali metal and alkaline earth metal hydrides such as lithium hydride, sodium hydride, potassium hydride and calcium hydride,
alkali metal amides such as lithium amide, sodium amide and potassium amide,
alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate;
alkali metal and alkaline earth metal phosphates such as potassium phosphate, calcium phosphate;
and furthermore organic bases,
such as tertiary amines such as trimethylamine, triethylamine, diisopropylethylamine and N-methylpiperidine, pyridine, substituted pyridines such as collidinge, lutidine, N-methylmorpholine and 4-dimethylaminopyridine and also bicyclic amines.

Examples of suitable nitrogen-containing bases are
$C_1$-$C_6$-alkylamines, preferably trialkylamines, for example triethylamine, trimethylamine, N-ethyl-diisopropylamine;
ammonia, pyridine, lutidine, collidine, 4-(dimethylamino) pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal hydroxides, and other metal hydroxides as described above.

Especially preferred bases are sodium hydroxide, potassium hydroxide and calcium hydroxide.

The term base as used herein also includes mixtures of two or more, preferably two of the above compounds. Particular preference is given to the use of one base.

The reaction mixture can then be further worked up by the methods customary therefor. In general, the phases are separated and the solvent used will be removed by customary processes, for example by distillation. For further purification, the customary processes such as for example crystallization (for example also by addition of a nonpolar solvent such as pentane, cyclohexane, heptane or toluene, or mixtures of the solvents mentioned) can be employed.

The preferred embodiments of the invention mentioned herein below have to be understood as being preferred either independently from each other or in combination with one another.

According to a preferred embodiment of the invention preference is also given to the preparation of those fluoroaromatics of formula (I), wherein the variables, either independently of one another or in combination with one another, have the following meanings:

A is preferably aryl, which is unsubstituted or substituted by one to five substituents selected from the group consisting of halogen, $C_1$-$C_6$-alkyl, $C_2$-$C_6$-alkenyl, $C_2$-$C_6$-alkynyl, $C_1$-$C_6$-haloalkyl, $C_3$-$C_6$-haloalkenyl, $C_3$-$C_6$-haloalkynyl, hydroxy, $C_1$-$C_6$-alkoxy, amino, ($C_1$-$C_6$-alkyl)amino and di($C_1$-$C_6$-alkyl)amino;
particularly preferred phenyl, which is unsubstituted or substituted by one to five substituents selected from the group consisting of halogen, $C_1$-$C_6$-alkyl, $C_2$-$C_6$-alkenyl, C₂-C₆-alkynyl, C₁-C₆-haloalkyl, C₃-C₆-haloalkenyl, C₃-C₆-haloalkynyl, hydroxy, C₁-C₆-alkoxy, amino, (C₁-C₆-alkyl)amino and di(C₁-C₆-alkyl)amino;
especially preferred phenyl, which is unsubstituted or substituted by one to three substituents selected from the group consisting of halogen, C₁-C₆-alkyl, C₁-C₆-haloalkyl, hydroxy and C₁-C₆-alkoxy;
more preferred phenyl, which is unsubstituted or substituted by one or two substituents selected from hydroxy;
also more preferred phenyl, which is unsubstituted or substituted by one substituent selected from the group consisting of halogen, C₁-C₆-alkyl, C₁-C₆-haloalkyl, hydroxy and C₁-C₆-alkoxy;
even more preferred phenyl, which is unsubstituted;
also even more preferred phenyl, which is substituted by one substituent selected from the group consisting of halogen, C₁-C₆-alkyl, C₁-C₆-haloalkyl, hydroxy and C₁-C₆-alkoxy.

A is also preferably phenyl, which substituted by one to five substituents selected from the group consisting of halogen, C₁-C₆-alkyl, C₂-C₆-alkenyl, C₂-C₆-alkynyl, C₁-C₆-haloalkyl, C₃-C₆-haloalkenyl, C₃-C₆-haloalkynyl, hydroxy, C₁-C₆-alkoxy, amino, (C₁-C₆-alkyl)amino and di(C₁-C₆-alkyl)amino;
particularly preferred phenyl, which is substituted by one to five substituents selected from the group consisting of halogen, C₁-C₆-alkyl, C₁-C₆-haloalkyl, hydroxy, C₁-C₆-alkoxy, amino, (C₁-C₆-alkyl)amino and di(C₁-C₆-alkyl)amino;
especially preferred phenyl, which is substituted by one to three substituents selected from the group consisting of halogen, C₁-C₆-alkyl, C₁-C₆-haloalkyl, hydroxy and C₁-C₆-alkoxy;
more preferred phenyl, which is substituted by one or two substituents selected from hydroxy.

A is preferably 5- or 6-membered heteroaryl, which is unsubstituted or substituted by one to four substituents selected from the group consisting of halogen, C₁-C₆-alkyl, C₂-C₆-alkenyl, C₂-C₆-alkynyl, C₁-C₆-haloalkyl, C₃-C₆-haloalkenyl, C₃-C₆-haloalkynyl, hydroxy, C₁-C₆-alkoxy, amino, (C₁-C₆-alkyl)amino and di(C₁-C₆-alkyl)amino;
particularly preferred 6-membered heteroaryl, which is unsubstituted or substituted by one to four substituents selected from the group consisting of halogen, C₁-C₆-alkyl, C₂-C₆-alkenyl, C₂-C₆-alkynyl, C₁-C₆-haloalkyl, C₃-C₆-haloalkenyl, C₃-C₆-haloalkynyl, hydroxy, C₁-C₆-alkoxy, amino, (C₁-C₆-alkyl)amino and di(C₁-C₆-alkyl)amino;
especially preferred pyridyl, which is unsubstituted or substituted by one to three substituents selected from the group consisting of halogen, C₁-C₆-alkyl, C₁-C₆-haloalkyl, hydroxy and C₁-C₆-alkoxy;
more preferred pyridyl, which is unsubstituted or substituted by one substituent selected from the group consisting of halogen, C₁-C₆-alkyl, C₁-C₆-haloalkyl, hydroxy and C₁-C₆-alkoxy;
even more preferred pyridyl, which is unsubstituted;
also even more preferred pyridyl, which is substituted by one substituent selected from the group consisting of halogen, C₁-C₆-alkyl, C₁-C₆-haloalkyl, hydroxy and C₁-C₆-alkoxy.

Particular preference is given to the preparation of fluoroaromatics of formula (1.1) to (1.20) of Table A listed below:

TABLE A

| No. | A |
|---|---|
| I.1 | phenyl |
| I.2 | 2-chloro-phenyl |
| I.3 | 3-chloro-phenyl |
| I.4 | 2-bromo-phenyl |
| I.5 | 3-bromo-phenyl |
| I.6 | 2-methyl-phenyl |
| I.7 | 3-methyl-phenyl |
| I.8 | 4-methyl-phenyl |
| I.9 | 3,5-(dimethyl)-phenyl |
| I.10 | 3-chloro-4-methyl-phenyl |
| I.11 | 3-chloro-2-methyl-phenyl |
| I.12 | 3-hydroxy-phenyl |
| I.13 | 3,5-(dihydroxy)-phenyl |
| I.14 | 4-methoxy-phenyl |
| I.15 | 3-hydroxycarbonyl |
| I.16 | 4-hydroxycarbonyl |
| I.17 | 2-amino-phenyl |
| I.18 | 3-amino-phenyl |
| I.19 | 4-amino-phenyl |
| I.20 | 2-pyridyl |

More particular preference is given to the preparation of fluoroaromatics of formulae (I.1), (I.3), (I.5), (I.6), (I.7), (I.8), (I.9), (I.10), (I.11), (I.12), (I.18), (I.19) and (I.20) as defined above.

Very particular preference is given to the preparation of fluoroaromatics of formula I.12:

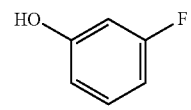

(I.12)

The aminoaromatics of formula (II) necessary for the process according to the invention are commercially available or can be prepared by known methods.

The invention is illustrated by the following examples without being limited thereto or thereby.

EXAMPLE 1

70 g (0.64 mol) 3-aminophenol were placed in 310 g (15.5 mol) anhydrous HF. 48.7 g (0.71 mol) NaNO₂ solved in 77 g H₂O were added over the course of 60 min at −10 to 0° C. to the aminophenol/HF mixture. Upon complete addition the suspension was then heated to 20° C. and, upon starting of the exothermic decomposition, the reaction temperature was increased to 52° C. After completion of the reaction (N₂ liberation was finished) the mixture was stirred another 60 min at 40° C. The slurry was cooled to 5° C. and 450 g H₂O was added while cooling. The mixture was extracted five times with 200 g dichloromethane. Brine was added to the combined organic phases and the pH adjusted to 4.3 with 40% KOH solution. After phase split, the organic layer was dried with MgSO₄ and the remaining dichloromethane was removed with heating under vacuum. The product was purified by distillation at 18-23 mbar/68-85° C.

46.5 g of 3-fluorophenol as a slightly yellow liquid with a purity of 92% (determined by quantitative HPLC: column: Zorbax Eclipse XDB-C18 1.8 μm 50*4.6 mm (Agilent®); eluent: water/acetonitrile with 0.1 vol-% H₃PO₃; retention time: 2.52 min) was obtained (yield: 59.6%).

EXAMPLE 2

70 g (0.64 mol) 3-aminophenol were placed in 340 g (17.0 mol) anhydrous HF. 48.7 g (0.71 mol) NaNO₂ solved in 77 g H₂O were added over the course of 60 min at −8 to −2° C. to the aminophenol/HF mixture. Upon complete addition the suspension was then heated to 50° C. and, upon starting of the exothermic decomposition, the reaction temperature was increased to 65° C. After completion of the reaction ($N_2$ liberation was finished) the mixture was stirred another 60 min at 55° C. The slurry was cooled to 5° C. and 150 g $H_2O$ and 150 ml KOH 40% were added. The mixture was transferred to a polymer coated reactor and the pH of the mixture was adjusted with 40% KOH to 4.4. The slurry then was extracted three times with 300 g MTBE. Brine was added to the combined organic phases and the pH adjusted to 4.3 with 40% KOH solution. After phase split, the organic layer was dried with $MgSO_4$ and the remaining MTBE was removed with heating under vacuum. The product was purified by distillation at 10-15 mbar/60-75° C.

47.4 g of 3-fluorophenol as a slightly yellow liquid with a purity of 86% (determined by quantitative HPLC: column: Zorbax Eclipse XDB-C18 1.8 μm 50*4.6 mm (Agilent®); eluent: water/acetonitrile with 0.1 vol-% $H_3PO_3$; retention time: 2.52 min) was obtained (yield: 57.6%).

EXAMPLE 3

70 g (0.64 mol) 3-aminophenol were placed in 340 g (17.0 mol) anhydrous HF. 46.3 g (0.67 mol) $NaNO_2$ solved in 77 g $H_2O$ were added over the course of 60 min at −10 to −1° C. to the aminophenol/HF mixture. Upon complete addition the suspension was then heated to 50° C. and, upon starting of the exothermic decomposition, the reaction temperature was increased to 62° C. After completion of the reaction ($N_2$ liberation was finished) the mixture was stirred another 60 min at 63° C. The slurry was cooled to 5° C. and 500 g $H_2O$ were added. The mixture was distilled with steam at 106-108° C. In total, 1159 g of the water/product mixture were removed by distillation. The distillate was then cooled to 25° C. and extracted three times with methoxypentane. $H_2O$ was added to the combined organic phases and the pH was adjusted to 4.2 with 30% KOH solution. After phase split, the organic layer was dried azeotropically and the remaining methoxypentane was removed with heating under vacuum. The product was purified by distillation at 18-23 mbar/68-85° C.

44.6 g of 3-fluorophenol as a slightly yellow liquid with a purity of 86% (determined by quantitative HPLC: column: Zorbax Eclipse XDB-C18 1.8 μm 50*4.6 mm (Agilent®); eluent: water/acetonitrile with 0.1 vol-% $H_3PO_3$; retention time: 2.52 min) was obtained (yield: 53.5%).

EXAMPLE 4

71.3 g (0.64 mol) 3-aminophenol (purity 98%) were placed in 340 g (17.0 mol) anhydrous HF.

48.6 g (0.7 mol) $NaNO_2$ solved in 77 g $H_2O$ were added over the course of 60 min at −10 to −1° C. to the aminophenol/HF mixture. Upon complete addition the suspension was then heated carefully to 27° C. and, upon starting of the exothermic decomposition, the reaction temperature was increased to 57° C. After completion of the reaction ($N_2$ liberation was finished) the mixture was stirred another 75 min without cooling or heating. The slurry was cooled to 10° C. and 400 g $H_2O$ were added. The mixture was distilled off at 106-108° C. In total, 321 g of the water/product mixture were removed by distillation. The distillate was then cooled to 25° C. and extracted five times with 70 g dichloromethane. Brine was added to the combined organic phases and the pH was adjusted to 4.3 with 40% KOH solution. After phase split, the organic layer was dried with $MgSO_4$ and the remaining dichloromethane was removed with heating under vacuum.

35.5 g of 3-fluorophenol as a slightly yellow liquid with a purity of 98.2% (determined by quantitative HPLC: column: Zorbax Eclipse XDB-C18 1.8 μm 50*4.6 mm (Agilent®); eluent: water/acetonitrile with 0.1 vol-% $H_3PO_3$; retention time: 2.52 min) was obtained (yield: 48.6%).

The remaining slurry from the first distillation was cooled to 60° C. and 400 g $H_2O$ were added once again. The mixture was distilled off at 106-108° C. In total, 447 g of the water/product mixture were removed by distillation. The distillate was then cooled to 25° C. and extracted five times with 70 g dichloromethane. Brine was added to the combined organic phases and the pH was adjusted to 4.3 with 40% KOH solution. After phase split, the organic layer was dried with $MgSO_4$ and the remaining dichloromethane was removed with heating under vacuum.

7.8 g of 3-fluorophenol as a slightly yellow liquid with a purity of 92.6% (determined by quantitative HPLC: column: Zorbax Eclipse XDB-C18 1.8 μm 50*4.6 mm (Agilent®); eluent: water/acetonitrile with 0.1 vol-% $H_3PO_3$; retention time: 2.52 min) was obtained (yield: 10.1%).

The remaining slurry from the second distillation was cooled to 60° C. and 400 g $H_2O$ were added once again. The mixture was distilled off once again at 106-108° C. In total, 567 g of the water/product mixture were removed by distillation. The distillate was then cooled to 25° C. and extracted five times with 70 g dichloromethane. Brine was added to the combined organic phases and the pH was adjusted to 4.3 with 40% KOH solution. After phase split, the organic layer was dried with $MgSO_4$ and the remaining dichloromethane was removed with heating under vacuum.

0.9 g of 3-fluorophenol as a slightly yellow liquid with a purity of 63.2% (determined by quantitative HPLC: column: Zorbax Eclipse XDB-C18 1.8 μm 50*4.6 mm (Agilent®); eluent: water/acetonitrile with 0.1 vol-% $H_3PO_3$; retention time: 2.52 min) was obtained (yield: 0.8%). The overall yield of the three fractions was 59.5%.

EXAMPLE 5

70 g (0.64 mol) 3-aminophenol were placed in 340 g (17.0 mol) anhydrous HF. 48.7 g (0.71 mol) solid $NaNO_2$ was added portion wise over the course of 60 min at −10 to −5° C. to the aminophenol/HF mixture. Upon complete addition the suspension is then heated to 50° C. and, upon starting of the exothermic decomposition, the reaction temperature was increased to 48° C. After completion of the reaction ($N_2$ liberation was finished) the mixture was stirred another 60 min at 54° C. The slurry was cooled to 5° C. and 550 g $H_2O$ were added. The mixture was distilled with steam at 106-108° C. In total, 1114 g of the water/product mixture were removed by distillation. The distillate was then cooled to 25° C. and extracted eight times with dichloromethane. $H_2O$ was added to the combined organic phases and the pH was adjusted to 4.2 with 30% KOH solution. After phase split, the organic layer was dried azeotropically and the remaining dichloromethane was removed with heating under vacuum.

32.8 g of 3-fluorophenol with a purity of 99% (determined by quantitative HPLC: column: Zorbax Eclipse XDB-$C_{18\ 1.8}$ μm 50*4.6 mm (Agilent®); eluent: water/acetonitrile with 0.1 vol-% $H_3PO_3$; retention time: 2.52 min) was obtained (yield: 45.6%).

EXAMPLE 6

70 g (0.64 mol) 3-aminophenol was placed in 340 g (17.0 mol) anhydrous HF. 48.7 g (0.71 mol) solid $NaNO_2$ was added portion wise over the course of 60 min at −10 to −5° C. to the aminophenol/HF mixture. Upon complete addition the suspension was then heated to 50° C. and, upon starting of the exothermic decomposition, the reaction temperature was increased to 43° C. After completion of the reaction ($N_2$ liberation was finished) the mixture was stirred another 60 min at 47° C. The slurry was cooled to 5° C. and 450 g $H_2O$ were added while cooling. The mixture was extracted five times with 250 g dichloromethane. Brine was added to the combined organic phases and the pH was adjusted to 4.3 with 40% KOH solution. After phase split, the organic layer was dried with $MgSO_4$ and the remaining dichloromethane was removed with heating under vacuum. The product was purified by distillation at 20 mbar/72-78° C.

32.9 g of 3-fluorophenol as a slightly yellow liquid with a purity of 97% (determined by quantitative HPLC: column: Zorbax Eclipse XDB-C18 1.8 μm 50*4.6 mm (Agilent®); eluent: water/acetonitrile with 0.1 vol-% $H_3PO_4$; retention time: 2.52 min) was obtained (yield: 44.3%).

EXAMPLE 7

(ACC. TO FERM ET AL.; J. OF AM. CHEM. SOC. 1950, 72, 4809)

13.6 g (0.12 mol) 3-aminophenol was placed in 25 g (1.25 mol) anhydrous HF. 6.5g (0.14 mol) solid $NaNO_2$ was added portion wise over the course of 60 min at −10 to −5° C. to the aminophenol/HF mixture. Upon complete addition the suspension was then heated to 28° C. and, upon starting of the exothermic decomposition, the reaction temperature increased very violently to 84° C. After completion of the reaction ($N_2$ liberation was finished) the mixture was stirred another 40 min at 40° C. The slurry was cooled to 5° C. and 80 g $H_2O$ were added while cooling.

The mixture was extracted five times with 100 g dichloromethane. Brine was added to the combined organic phases and the pH was adjusted to 4.3 with 40% KOH solution. After phase split, the organic layer was dried with $MgSO_4$ and the remaining dichloromethane was removed with heating under vacuum. The product was purified by distillation at 15 mbar/66-78° C.

4.3 g of 3-fluorophenol as a slightly yellow liquid with a purity of 89.0% (determined by quantitative HPLC: column: Zorbax Eclipse XDB-C18 1.8 μm 50*4.6 mm (Agilent®); eluent: water/acetonitrile with 0.1 vol-% $H_3PO_4$; retention time: 2.52 min) was obtained (yield: 28.5%).

EXAMPLE 8

15 g (0.14 mol) 3-aminophenol were placed under cooling in a mixture of 247.5 g (12.4 mol) anhydrous HF and 165 g (2.1 mol) pyridine. 10.4 g (0.15 mol) solid $NaNO_2$ is added portion wise over the course of 20 min at −12 to −8° C. to the aminophenol/HF/pyridine mixture. Upon complete addition the suspension is then heated to 60° C. and the exothermic decomposition starts. After completion of the reaction ($N_2$ liberation was finished) the mixture was stirred another 40 min at 60° C. The slurry was cooled to 5° C. and 500 g $H_2O$ were added with cooling.

The mixture was extracted three times with 250 g dichloromethane. Brine was added to the combined organic phases and the pH was adjusted to 4.3 with 40% KOH solution. After phase split, the organic layer was dried with $MgSO_4$ and the remaining dichloromethane was removed with heating under vacuum. The product is obtained as a slightly yellow liquid.

4.9 g of 3-fluorophenol with a purity of 87.2% (determined by quantitative HPLC: column: Zorbax Eclipse XDB-C18 1.8 μm 50*4.6 mm (Agilent®); eluent: water/acetonitrile with 0.1 vol-% $H_3PO_4$; retention time: 2.52 min;) was obtained (yield: 25.4%)

EXAMPLE 9

3-Aminophenol 70 g (0.64 mol) is placed in 310 g (17.0 mol) anhydrous HF.

60.6 g (0.71 mol) $KNO_2$ solved in 22 g $H_2O$ is added over the course of 45 min at −10 to −3° C. to the Aminophenol/HF mixture.

Upon complete addition the suspension is then heated to 50° C. and the exothermic decomposition starts. The reaction temperature is increased to 52° C. After completion of the reaction ($N_2$ liberation is finished) the mixture is stirred another 45 min at 55° C. The slurry is cooled to 5° C. and 450 g $H_2O$ added with cooling. The mixture is extracted five times with 200 g dichloromethane. Brine is added to the combined organic phases and the pH adjusted to 4.3 with 40% KOH solution. After phase split, the organic layer is dried with $MgSO_4$ and the remaining dichloromethane is removed with heating under vacuum. The product is purified by distillation at 18-23 mbar/68-85° C. and obtained as a slightly yellow liquid. Yield: 35.9 g; 85.6% purity according quantitative hplc, 42.7%.

The invention claimed is:

1. A process for manufacturing fluoroaromatics of formula (I), $$A\text{-}F \qquad (I)$$

wherein

A is aryl or 5- or 6-membered heteroaryl,
which independently from one another both are unsubstituted or substituted by one to five substituents selected from the group consisting of halogen, $C_1$-$C_6$-alkyl, $C_2$-$C_6$-alkenyl, $C_2$-$C_6$-alkynyl, $C_1$-$C_6$-haloalkyl, $C_3$-$C_6$-haloalkenyl, $C_3$-$C_6$-haloalkynyl, hydroxy, $C_1$-$C_6$-alkoxy, amino, ($C_1$-$C_6$-alkyl)amino and di ($C_1$-$C_6$-alkyl)amino;

comprising step a) diazotization of aminoaromatics of formula (II), $$A\text{-}NH_2 \qquad (II)$$

wherein A is defined as in formula (I);
in anhydrous HF with an aqueous solution of a diazotizing agent selected from nitrites; followed by step b) thermic decomposition of the diazonium salt of formula (III)

$$A\text{-}N_2^+F^- \qquad (III)$$

resulting from step a).

2. The process as claimed in claim 1, wherein diazotizing agent is selected from alkali metal nitrites.

3. The process as claimed in claim 2, wherein the diazotizing agent is selected from $NaNO_2$ and $KNO_2$.

4. The process as claimed in claim 2, wherein the diazotizing agent is selected from $NaNO_2$.

5. The process as claimed in claim 1, wherein the aminoaromatics of formula (II) and the HF are initially charged in a reaction vessel, and subsequently the aqueous solution of the diazotizing agent is added.

6. The process as claimed in claim 1, wherein step b) is carried out at a temperature from 15° C. to 55° C.

7. The process as claimed in claim 5, wherein the amount of HF used is from 10 to 30 mole equivalents based on the amount of aminoaromatics of formula (II).

8. The process as claimed in claim 5, wherein the amount of HF used is from 15 to 27 mole equivalents based on the amount of aminoaromatics of formula (II).

9. The process as claimed in claim 1, wherein after completion or partial completion of step b), the reaction mixture is worked up by steam distillation.

10. The process as claimed in claim 1, wherein after completion or partial completion of step b), the reaction mixture is worked up by steam distillation and the pH of the distillate resulting from steam distillation is adjusted to pH =2-7.

11. The process as claimed in claim 1, wherein A is phenyl, which is unsubstituted or substituted by one to five substituents selected from the group consisting of halogen, $C_1$-$C_6$-alkyl, $C_2$-$C_6$-alkenyl, $C_2$-$C_6$-alkynyl, $C_1$-$C_6$-haloalkyl, $C_3$-$C_6$-haloalkenyl, $C_3$-$C_6$-haloalkynyl, hydroxy, $C_1$-$C_6$-alkoxy, amino, ($C_1$-$C_6$-alkyl)amino and di ($C_1$-$C_6$-alkyl) amino.

12. The process as claimed in claim 1, wherein A is phenyl, unsubstituted or substituted by one or two substituents selected from hydroxy.

13. The process as claimed in claim 1, wherein A is 3-hydroxy-phenyl.

\* \* \* \* \*